United States Patent [19]
Yasushi

[11] Patent Number: 5,330,414
[45] Date of Patent: Jul. 19, 1994

[54] BRAIN WAVE INDUCING APPARATUS

[75] Inventor: Mitsuo Yasushi, Saitama, Japan

[73] Assignee: Pioneer Electronic Corporation, Tokyo, Japan

[21] Appl. No.: 833,937

[22] Filed: Feb. 11, 1992

[30] Foreign Application Priority Data

May 23, 1991 [JP] Japan ................ 3-118561

[51] Int. Cl.⁵ .............................. A61M 21/00
[52] U.S. Cl. ...................................... 600/27
[58] Field of Search ................... 600/26–28; 128/731–732, 905

[56] References Cited

U.S. PATENT DOCUMENTS

| | | | |
|---|---|---|---|
| 3,837,331 | 9/1974 | Ross | 600/27 |
| 3,884,218 | 5/1975 | Monroe | 600/28 |
| 3,893,450 | 7/1975 | Ertl | |
| 4,195,626 | 4/1980 | Schweizer | |
| 4,334,545 | 6/1982 | Shiga | 128/732 |

FOREIGN PATENT DOCUMENTS

| | | | |
|---|---|---|---|
| 0375106 | 6/1990 | European Pat. Off. | 128/732 |
| 412629 | 2/1991 | European Pat. Off. | |
| 2713891 | 10/1978 | Fed. Rep. of Germany | |
| 62-87165 | 4/1987 | Japan | |
| 1088607 | 10/1967 | United Kingdom | 600/28 |
| 2067410 | 7/1981 | United Kingdom | 600/28 |

Primary Examiner—Kyle L. Howell
Assistant Examiner—J. P. Lacyk
Attorney, Agent, or Firm—Sughrue, Mion, Zinn, Macpeak & Seas

[57] ABSTRACT

A random signal generator outputs a random noise signal to a band pass filter which selectively passes frequency components in the frequency range of a desired brain wave from a subject. The output of the band pass filter is supplied to an automatic level controller. The automatic level controller sets the output of band pass filter to a predetermined amplitude. Then, the output of the automatic level controller is fed to a stimulating light generator, which converts the output of the automatic level controller into a light signal for stimulating the subject in order to induce the desired brain wave from the subject. The light signal is then emitted into the subject's eyes.

10 Claims, 1 Drawing Sheet

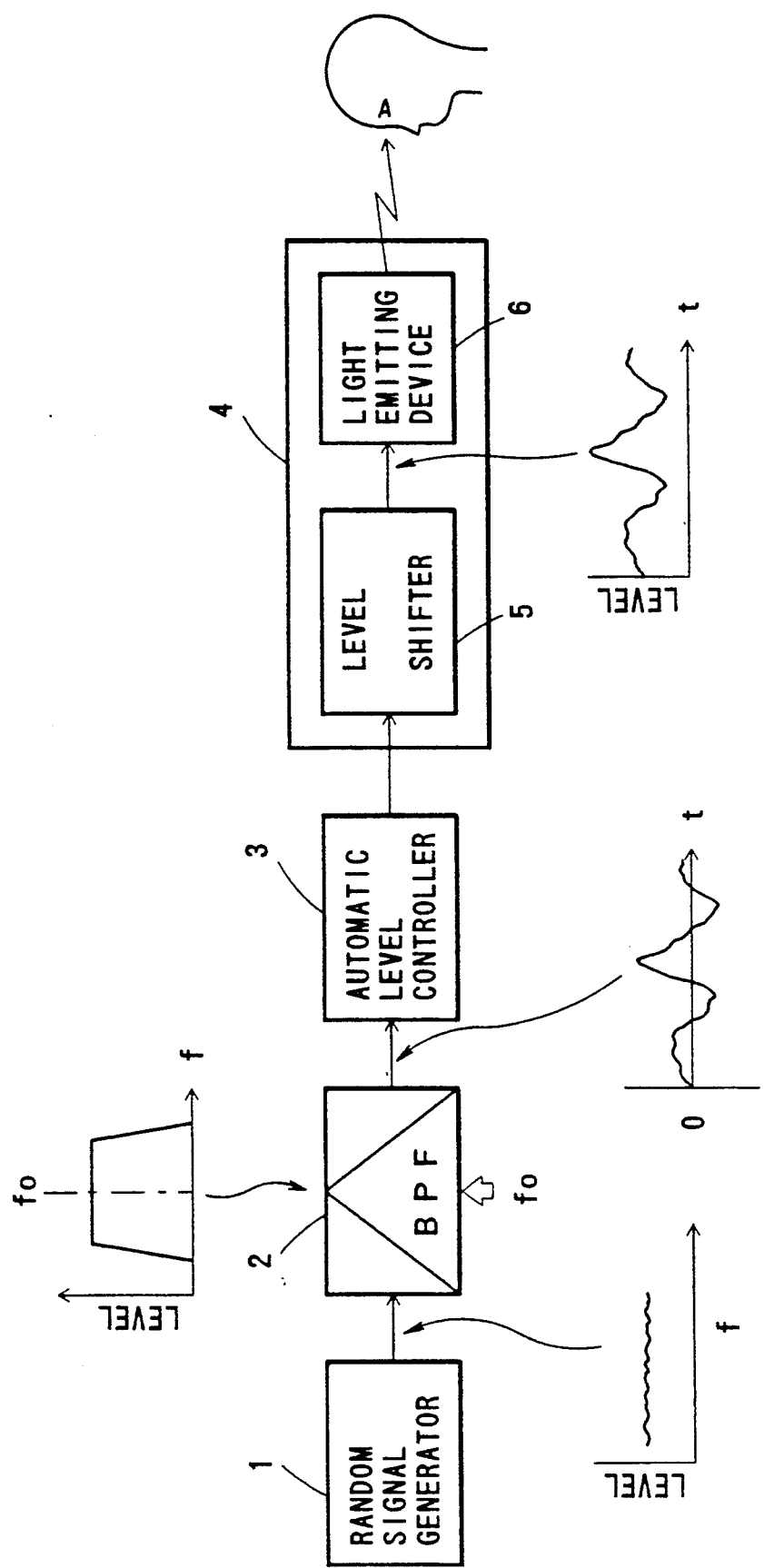

BRAIN WAVE INDUCING APPARATUS

BACKGROUND OF THE INVENTION

1. Field of the Invention

This invention relates to a brain wave inducing apparatus for inducing brain waves such as $\alpha$, $\beta$, and $\theta$ waves from a human body through optical stimulation.

2. Related Art

It is well known that there is a close relationship between the brain waves of a person and his or her biological, psychological conditions. For example, $\alpha$ waves (about 8–13 Hz) are dominantly developed when a person is relaxed, $\beta$ waves (about 14–30 Hz) are dominant when mentally and physically active, and $\theta$ waves (about 4–7 Hz) are dominant when the person is sleepy.

Conversely, if a specific brain wave is induced dominantly, then the person will enter the corresponding physical and psychological condition. Therefore, the use of the relationship between these brain waves and their corresponding physical, psychological conditions may be useful in controlling physical and psychological conditions in human beings.

Laid Open Japanese Patent Publication No. 62-87165 discloses a "relaxing apparatus." With this apparatus, a white noise outputted from a random signal generator is directed to a filter having a 1/f characteristic that produces a fluctuation signal of 1/f characteristic. A reference frequency set within the $\alpha$ frequency range (about 8–13 Hz) is frequency-modulated by the fluctuation signal. This frequency-modulated signal Vp drives a light emitting device to cycle on and off so as to produce a stimulating light whose time interval fluctuates with 1/f characteristic. Thereby, this stimulating signal is used to induce $\alpha$ waves in a patient. The frequency modulated signal Vp has a constant amplitude and a regular waveform.

$\alpha$ waves as well as other brain waves, are usually not uniform in waveform and amplitude. It is known that brain waves have a so-called "pull-in phenomenon" where a specific brain wave is "pulled in" or induced in response to an optical stimulation. When effectively inducing a specific brain wave by using the pull-in phenomenon, an optically stimulating signal should have a waveform as close to an actual brain wave as possible. From this point of view, the waveform of the frequency-modulated signal Vp of the relax apparatus disclosed by Laid Open Japanese Patent No. 62-87165 is too simple and not satisfactory. Thus, the use of the brain wave of a patient is the most efficient way of inducing a desired brain wave from that patient. However, picking up the brain waves from the patient will usually require electrodes and cords as well as many accessory circuits such as signal processing circuits, which makes the apparatus complex, large and burdensome.

SUMMARY OF THE INVENTION

An object of the present invention is to provide a brain wave inducing apparatus where a simple circuit configuration makes it possible to induce brain waves. A further object is to provide a brain wave inducing apparatus that uses an optically stimulating signal having a waveform that is more closely tied to actual brain waves than the related art discussed above.

According to the invention, a random signal generator outputs a random noise signal to a band pass filter which selectively passes frequency components in the frequency range of a brain wave to be induced from a subject. An automatic level controller sets the output of band pass filter to a predetermined amplitude. Then, a stimulating light generator converts the output of the automatic level controller into a light signal for stimulating the subject to induce the desired brain wave from the subject.

BRIEF DESCRIPTION OF THE DRAWINGS

Features and other objects of the invention will be more apparent from the description of the preferred embodiment with reference to FIG. 1, which shows a brain wave inducing apparatus according to the invention.

DETAILED DESCRIPTION OF THE PREFERRED EMBODIMENT

FIG. 1 is a block diagram of an embodiment of the present invention. The embodiment is described with respect to the induction of $\alpha$ waves. In the figure, a random signal generator 1 generates a random noise (so-called white noise) that contains a wide range of frequency components. The output of the random signal generator 1 is supplied to a band pass filter 2 whose center frequency may be shifted at will, so that frequency components corresponding to a desired brain wave, such as $\alpha$, $\beta$, or $\theta$ waves, is passed through. In this embodiment, the frequency components corresponding to $\alpha$ waves are passed through. The band pass filter can take the form of a known switched capacitor filter where a clock is varied to vary the center frequency fo of the pass band. A center frequency of 10.5 Hz, e.g. is selected for $\alpha$ waves, and the frequency components in the range of about 8–13 Hz pass through the band pass filter 2. Thus, the output of the band pass filter 2 is much closer to actual, desired brain waves than it is in the related art discussed above. The output of the band pass filter is input to an automatic level controller 3 which amplifies the frequency components corresponding to the $\alpha$ waves from the band pass filter 2 to a predetermined level and sends the result to a level shifter in a stimulating signal generator 4. The level shifter 5 outputs the output of the automatic level controller 3 as a drive signal whose amplitude has been shifted as depicted in FIG. 1, (by superimposing a DC component on the amplitude) so that the entire waveform of frequency components in the $\alpha$ waves is fully utilized in producing a stimulating light signal. The level shifter 5 sends an output thereof to a light emitting device 6 which controls a light emitting element such as an LED to vary intensity thereof in accordance with the drive signal from the level shifter 5 (intensity-modulated light signal). The output of light emitting device 6 goes into the eyes of the subject to stimulate the subject. In this manner, the $\alpha$ waves of the subject are induced while the subject watches the stimulating light.

If $\theta$ waves are to be induced, the center frequency fo of the band pass filter 2 is set to, e.g. 5.5 Hz, which is a mid-frequency in the range of about 4–7 Hz. If the desired brain waves are $\beta$ waves then the center frequency of the band pass filter 2 is set, e.g., to 22 Hz which is a mid-frequency in the range of about 14–30 Hz.

The center frequency of the band pass filter 2 suitable for inducing a desired brain wave may vary slightly from subject to subject. Thus, if the optimum center frequency is previously known for a particular subject then the center frequency may be preset to that known frequency for more effective brain wave induction.

A brain wave inducing apparatus according to the invention does not require electrodes and cords for picking up a subject's brain waves, or circuits for processing such brain waves. This greatly simplifies the overall circuit configuration of the circuit providing the stimulating light.

What is claimed is:

1. A brain wave inducing apparatus for inducing desired brain waves from a subject, comprising:
    a random signal generator for outputting a random noise signal;
    a band pass filter for receiving the random noise signal and selectively passing frequency components that lie in a frequency range of the desired brain waves;
    an automatic level controller for setting the frequency components of said band pass filter to a predetermined amplitude;
    a stimulating light generator for converting the output of said automatic level controller into a light signal for stimulating the subject to induce the desired brain waves from the subject.

2. A brain wave inducing apparatus according to claim 1, wherein the light signal is intensity modulated.

3. A brain wave inducing apparatus according to claim 1, wherein said random noise signal is a white noise.

4. A brain wave inducing apparatus according to claim 1, wherein said band pass filter has a center frequency that is a mid frequency in the frequency range of the desired brain waves, and said band pass filter sets the center frequency in accordance with an input signal supplied to said band pass filter.

5. A brain wave inducing apparatus according to claim 1, wherein said stimulating light generator comprises a level shifter for shifting an amplitude of the output of said automatic level controller, and a light emitting device for outputting the light signal, which light signal varies in intensity in accordance with an output of said level shifter.

6. A brain wave inducing apparatus according to claim 4, wherein the center frequency set by said band pass filter lies within the range of 8-13 Hz to induce $\alpha$ waves as the desired brain waves.

7. A brain wave inducing apparatus according to claim 4, wherein the center frequency set by said band pass filter lies within the range of 14-30 Hz to induce $\beta$ waves as the desired brain waves.

8. A brain wave inducing apparatus according to claim 4, wherein the center frequency set by said band pass filter lies within the range of 4-7 Hz to induce $\Theta$ waves as the desired brain waves.

9. A brain wave inducing apparatus according to claim 4, wherein the center frequency set by said band pass filter is determined by obtaining optimum center frequency data from a particular subject.

10. A brain wave inducing apparatus according to claim 4, wherein said band pass filter comprises a switched capacitor filter and a clock for setting the center frequency.

* * * * *